United States Patent
Fazzi et al.

(10) Patent No.: US 10,349,883 B2
(45) Date of Patent: Jul. 16, 2019

(54) AIRWAY IMPEDANCE MEASUREMENT INTEGRATED WITH RESPIRATORY TREATMENT DEVICES

(71) Applicant: KONINKLIJKE PHILIPS N.V., Eindhoven (NL)

(72) Inventors: Alberto Fazzi, Eindhoven (NL); Teunis Johannes Vink, Valkenswaard (NL); Dirk Erneset Von Hollen, Clark, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 850 days.

(21) Appl. No.: 14/360,036

(22) PCT Filed: Dec. 18, 2012

(86) PCT No.: PCT/IB2012/057417
§ 371 (c)(1),
(2) Date: May 22, 2014

(87) PCT Pub. No.: WO2013/098714
PCT Pub. Date: Jul. 4, 2013

(65) Prior Publication Data
US 2014/0309546 A1    Oct. 16, 2014

Related U.S. Application Data

(60) Provisional application No. 61/581,718, filed on Dec. 30, 2011.

(51) Int. Cl.
*A61B 5/08*    (2006.01)
*A61B 5/00*    (2006.01)
(Continued)

(52) U.S. Cl.
CPC ............ *A61B 5/4836* (2013.01); *A61B 5/085* (2013.01); *A61B 5/087* (2013.01); *A61B 5/72* (2013.01);
(Continued)

(58) Field of Classification Search
CPC ........... A61B 5/00; A61B 5/085; A61B 5/087; A61B 5/4836; A61B 5/72; A61M 16/00;
(Continued)

(56) References Cited

U.S. PATENT DOCUMENTS

| 5,522,397 A | 6/1996 | Vermaak |
| 5,876,352 A * | 3/1999 | Weismann ............. A61B 5/085 600/529 |

(Continued)

FOREIGN PATENT DOCUMENTS

| DE | 19809867 C1 | 9/1999 |
| DE | 102006011900 A1 | 9/2007 |

(Continued)

OTHER PUBLICATIONS

Gappa et al, "Passive Respiratory Mechanics: The Occlusion Techniques", European Respiratory Journal, vol. 17, No. 1, Jan. 1, 2001, pp. 141-148.

(Continued)

*Primary Examiner* — Eric J Messersmith
(74) *Attorney, Agent, or Firm* — Michael W. Haas

(57) ABSTRACT

Airway impedance of a subject using a respiratory treatment device can be measured, in accordance with one or more embodiments. A conduit is configured to communicate a flow of inhaled gas and a flow of exhaled gas to and from an airway of the subject using the respiratory treatment device. A first valve is disposed within the conduit and configured to affect the flow of exhaled gas. One or more sensors are disposed within the conduit and are configured to provide a (Continued)

signal conveying information associated with one or more characteristics of gas exhaled by the subject while the flow of exhaled gas is affected or unaffected by the first valve. An airway impedance monitoring module can be executed by a processor to determine an impedance metric of the airway of the subject based on the information conveyed by the signal provided by the one or more sensors.

20 Claims, 8 Drawing Sheets

(51) Int. Cl.
| | |
|---|---|
| *A61B 5/085* | (2006.01) |
| *A61B 5/087* | (2006.01) |
| *A61M 11/00* | (2006.01) |
| *A61M 15/00* | (2006.01) |
| *A61M 16/08* | (2006.01) |
| *A61M 16/00* | (2006.01) |
| *A61M 16/20* | (2006.01) |
| *A61M 11/02* | (2006.01) |
| *A61M 16/06* | (2006.01) |

(52) U.S. Cl.
CPC ............ *A61M 11/00* (2013.01); *A61M 15/00* (2013.01); *A61M 16/0006* (2014.02); *A61M 16/024* (2017.08); *A61M 16/0816* (2013.01); *A61M 16/0883* (2014.02); *A61M 16/202* (2014.02); *A61M 16/205* (2014.02); *A61M 11/02* (2013.01); *A61M 15/0015* (2014.02); *A61M 15/0016* (2014.02); *A61M 15/0086* (2013.01); *A61M 16/06* (2013.01); *A61M 16/0833* (2014.02); *A61M 16/208* (2013.01); *A61M 2016/0021* (2013.01); *A61M 2016/0027* (2013.01); *A61M 2016/0036* (2013.01); *A61M 2016/0042* (2013.01); *A61M 2230/46* (2013.01)

(58) Field of Classification Search
CPC .. A61M 16/08; A61M 16/20; A61M 16/0006; A61M 16/0883; A61M 16/202; A61M 11/00; A61M 15/00; A61M 16/0051; A61M 16/0816; A61M 16/201
See application file for complete search history.

(56) References Cited

U.S. PATENT DOCUMENTS

| | | |
|---|---|---|
| 8,459,258 B2 | 6/2013 | Slessarev |
| 2002/0020410 A1 | 2/2002 | Rydin et al. |
| 2012/0289852 A1 | 11/2012 | Van Den Aardweg |
| 2013/0102917 A1* | 4/2013 | Colbaugh ............ A61M 16/00 600/533 |

FOREIGN PATENT DOCUMENTS

| | | |
|---|---|---|
| JP | H06343623 A | 12/1994 |
| JP | 2002143309 A | 5/2002 |
| JP | 2009502265 A | 1/2009 |
| WO | 2011067698 A1 | 6/2011 |

OTHER PUBLICATIONS

Oostveen et al, "The Forced Oscillation Technique in Clinical Practice: Methodology, Recommendations and Future Developments", European Respiratory Journal, vol. 22, 2003, pp. 1026-1041.
http://www.thorasys.com, Thoracic Medical Systems Inc., Tremoflo Airwave Oscillometry System, Downloaded May 21, 2014.
http://www.thorasys.com, Thoracic Medical Systems Inc., Tremoflo C-100 Technical Specifications, Downloaded May 21, 2014.
http://www.pontesmedical.com, Pontes Medical, Downloaded May 21, 2014.

* cited by examiner

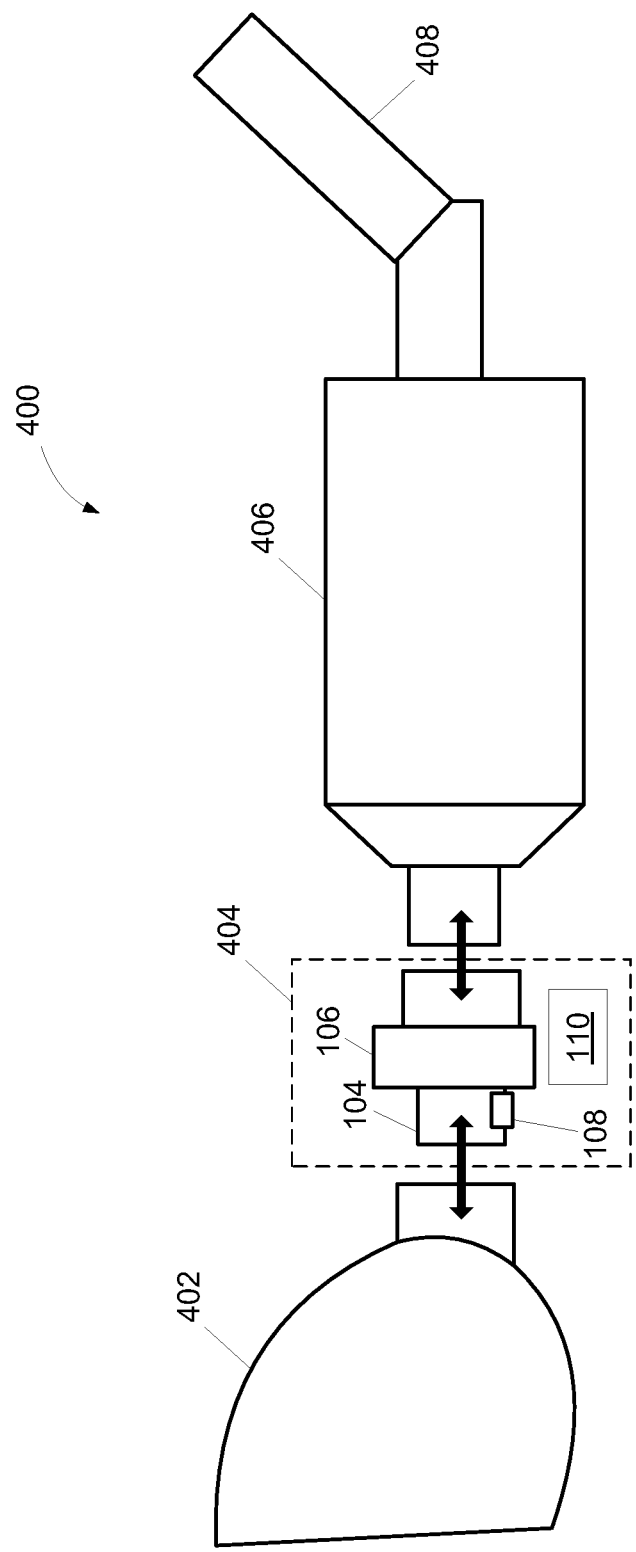

AIRWAY IMPEDANCE MEASUREMENT INTEGRATED WITH RESPIRATORY TREATMENT DEVICES

CROSS-REFERENCE TO PRIOR APPLICATIONS

This application is the U.S. National Phase application under 35 U.S.C. § 371 of International Application No. PCT/IB2012/057417, filed on Dec. 18, 2012, which claims the benefit of U.S. Provisional Patent Application No. 61/581,718, filed on Dec. 30, 2011. These applications are hereby incorporated by reference herein.

The present disclosure pertains to measuring airway impedance of a subject using a respiratory treatment device.

It is well known to measure airway impedance. However, existing approaches typically involve the use of standalone devices and are generally applied for diagnostic purposes.

Accordingly, it is an object of one or more embodiments of the present invention to provide a system integrated with a respiratory treatment device that is configured to measure airway impedance. The system comprises a conduit, a first valve, one or more sensors, and one or more processors. The conduit is configured to provide a flow path for gas toward and away from an airway of a subject using the respiratory treatment device during inhalation and exhalation, respectively. The first valve is disposed within the conduit to affect gas flow through the flow path formed by the conduit. The one or more sensors are disposed within the conduit and configured to provide a signal conveying information associated with one or more characteristics of gas in the flow path formed by the conduit while the gas flow through the flow path is affected or unaffected by the first valve. The one or more processors are configured to execute one or more computer program modules. The one or more computer program modules include an airway impedance monitoring module (120) configured to determine an impedance metric of the airway of the subject based on the signal provided by the one or more sensors during the one or more exhalations for which gas flow through the flow path is affected or unaffected by the first valve.

It is yet another aspect of one or more embodiments of the present invention to provide a method for measuring airway impedance of a subject using a respiratory treatment device. The method includes providing a flow path for gas toward and away from an airway of a subject using the respiratory treatment device during inhalation and exhalation, respectively. The method includes affecting gas flow through the flow path. The method includes providing a signal conveying information associated with one or more characteristics of gas in the flow path while the gas flow through the flow path is affected or unaffected. The method includes determining an impedance metric of the airway of the subject based on the signal during the one or more exhalations for which gas flow through the flow path is affected or unaffected.

It is yet another aspect of one or more embodiments to provide a system integrated with a respiratory treatment device and configured to measure airway impedance. The system comprises fluid communication means, first valve means, sensing means, and processing means. The fluid communication means is configured to provide a flow path for gas toward and away from an airway of a subject using the respiratory treatment device during inhalation and exhalation, respectively. The first valve means is disposed within the fluid communication means to affect gas flow through the flow path formed by the fluid communication means. The sensing means is disposed within the fluid communication means and configured to provide a signal conveying information associated with one or more characteristics of gas in the flow path formed by the fluid communication means while the gas flow through the flow path is affected or unaffected by the first valve means. The processing means is configured to execute one or more computer program modules. The one or more computer program modules include an airway impedance monitoring module configured to determine an impedance metric of the airway of the subject based on the signal provided by the sensing means during the one or more exhalations for which gas flow through the flow path is affected or unaffected by the first valve means.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

FIGS. 4A, 4B, 4C, and 4D illustrate exemplary embodiments of airway impedance measurement capabilities integrated with a respiratory treatment device.

Figure 5:
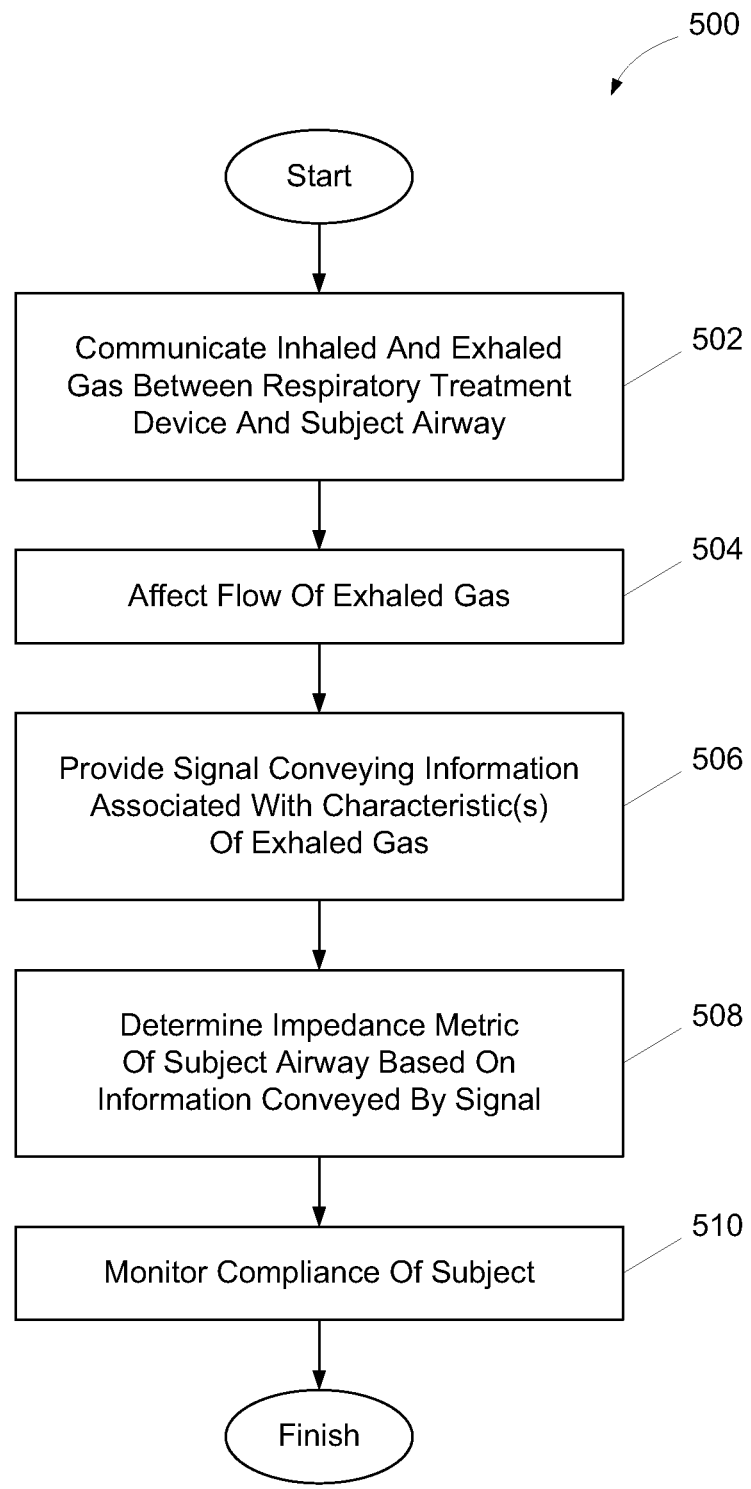

FIG. 5 illustrates a method for measuring airway impedance of a subject using a respiratory treatment device, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Exemplary embodiments of the present invention may provide an easy-to-use, yet accurate evaluation of lung function by incorporating the measurement of lung and/or airway impedance in devices commonly used for respiratory treatment. By way of non-limiting example, respiratory treatment devices may include inhalers, nebulizers, ventilators, positive airway pressure devices, valved holding chambers, spacers, and/or other respiratory treatment devices. Some respiratory treatment devices may be configured to facilitate drug inhalation, support respiration, and/or treat various respiratory disorders.

Incorporating the measurement of lung and/or airway impedance in devices commonly used for respiratory treatment may provide for daily monitoring of lung function and/or monitoring of trends in subject condition. Daily monitoring of lung function may provide advantages in tuning treatment for subjects affected by different types of lung disease, in verifying the efficacy of the treatment, in supporting the development of new medications and/or treatments, and/or in other manners associated with respiratory treatment. Additionally, by integrating monitoring technologies in the device providing the treatment, regular monitoring can be performed without additional burden for the subject and/or with a lower risk with respect to lack of use of the device.

Figure 1:
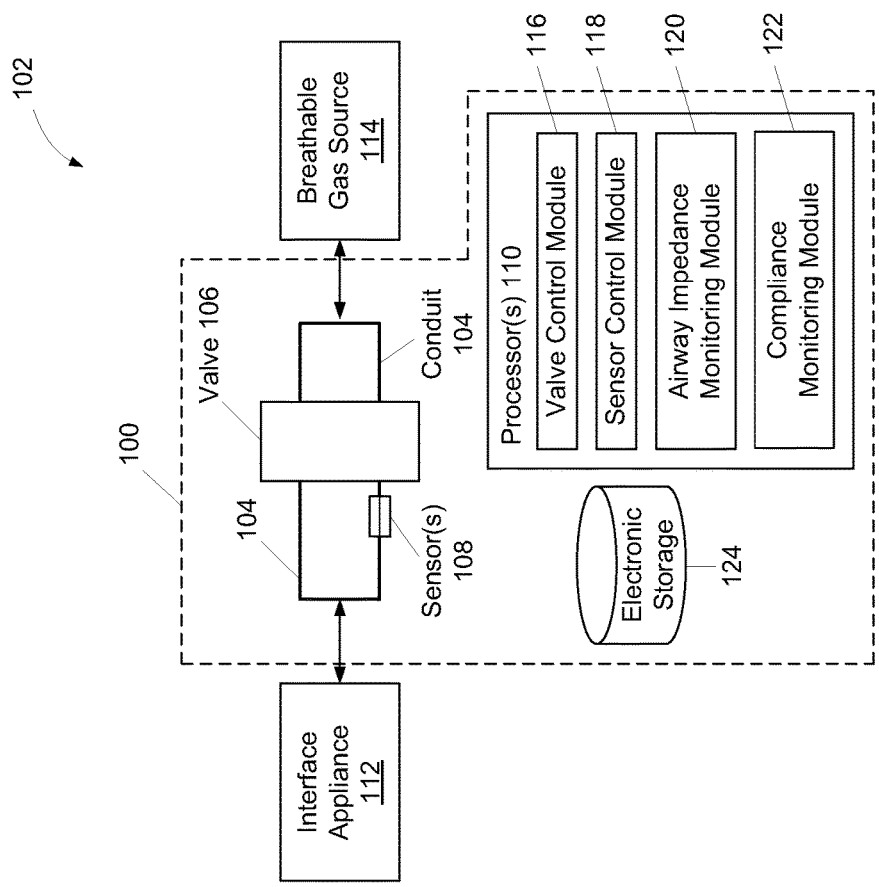
FIG. 1 illustrates a system integrated with a respiratory treatment device and configured to measure airway impedance, in accordance with one or more embodiments.

FIG. 1 illustrates a system 100 integrated with a respiratory treatment device 102 and configured to measure airway impedance, in accordance with one or more embodiments. As depicted in FIG. 1, system 100 includes a conduit 104, a valve 106, one or more sensors 108, one or more processors 110, and/or other components. The depiction in FIG. 1 of system 100 and respiratory treatment device 102 is not intended to be limiting as system 100 and/or respiratory treatment device 102 may include more or less components than those shown. For example, respiratory treatment device 102 may include a spacer and/or a valved holding chamber to help subject coordinate an inhalation/expiration process. As another example, one or more components of system 100 and/or respiratory treatment device 102 may be integrated as a single component.

The conduit 104 may include a tube, piping, and/or other conduits. The conduit 104 is configured to provide a flow path for gas toward and away from an airway of a subject using the respiratory treatment device during inhalation and exhalation, respectively. That is, conduit 104 is configured to communicate a flow of inhaled gas and a flow of exhaled gas. In some embodiments, conduit 104 includes two or more branches. One or more of the branches may be dedicated to communicating the flow of exhaled gas. Exemplary embodiments having a branched conduit are described further in connection with FIG. 4B.

In some embodiments, conduit 104 is disposed proximate to an interface appliance 112. The interface appliance 112 is configured to provide fluid communication between respiratory treatment device 102 and an airway of a subject using respiratory treatment device 102. Some examples of interface appliance 112 may include, for example, an endotracheal tube, a nasal cannula, a nasal mask, a nasal/oral mask, a full face mask, a total face mask, or other interface appliances configured to provide fluid communication with an airway of a subject.

The conduit 104 may be in fluid communication with a breathable gas source 114. The breathable gas source 114 may be configured to provide some or all of the flow of inhaled gas. Some examples of breathable gas source 114 may include the ambient atmosphere surrounding respiratory treatment device 102, a gas tank, a pump, a source of a breathable substance, and/or other sources of breathable gas.

The valve 106 is disposed within conduit 104 to affect gas flow through the flow path formed by the conduit. In some embodiments, valve 106 is configured to affect the flow of exhaled gas. According to various embodiments, affecting the flow of exhaled gas may include temporarily interrupting the flow of exhaled gas, providing a time-variable resistance to the flow of exhaled gas, and/or otherwise affecting the flow of exhaled gas.

In accordance with some embodiments, valve 106 may include an interrupter valve configured to temporarily interrupt the flow of exhaled gas communicated by the conduit. Such an interrupter valve may be configured to interrupt the flow of exhaled gas for a predetermined period of time or until a detected pressure of the exhaled gas becomes stable. In some embodiments, valve 106 includes a passive valve having a predetermined oscillation frequency. By way of non-limiting example, a predetermined oscillation frequency may include a resonant frequency and/or other frequencies. The passive valve may be configured to provide a time-variable resistance to the flow of exhaled gas. Embodiments including an interrupter valve or a passive valve are described further herein.

The sensor(s) 108 are disposed within conduit 104, valve 106, and/or respiration interface 112. The sensor(s) 108 are configured to provide a signal conveying information associated with one or more characteristics of gas in the flow path formed by the conduit, such as gas inhaled and/or exhaled by the subject. Such characteristics may include one or more of a flow rate of gas communicated by conduit 104, a gas pressure within conduit 104, a volume or amount of gas communicated by conduit 104, and/or other characteristics of the inhaled and/or the exhaled gas. The characteristics of the exhaled gas may include those observable while the flow of exhaled gas is affected or unaffected by valve 106. Some examples of sensor(s) 108 include one or more of a flow sensor, a pressure sensor, and/or other sensors. A flow sensor may be configured to provide a signal conveying information associated with a flow rate of gas communicated by conduit 104. A pressure sensor may be configured to provide a signal conveying information associated with a gas pressure within conduit 104. A pressure sensor may provide a signal conveying information associated with pressure referred to atmospheric pressure, or with absolute pressure. In the case of absolute pressure, a second pressure sensor may be disposed elsewhere in system 100 to provide a reference signal conveying information associated with atmospheric pressure.

The processor(s) 110 are configured to execute one or more computer program modules. The one or more computer program modules include a valve control module 116, a sensor control module 118, an airway impedance monitoring module 120, a compliance monitoring module 122, and/or other modules.

The valve control module 116 is configured to control valve 106. The valve control module 116 may be configured to control valve 106 to affect gas flow through the flow path formed by conduit 104 during one or more exhalations by the subject. In some embodiments, controlling valve 106 includes causing valve 106 to temporarily interrupt the flow of exhaled gas communicated by conduit 104. The valve control module 116 may time the occlusion start and release in order to synchronize or coordinate with an exhalation phase of the subject. That is, valve control module 116 may be configured to synchronize affecting gas flow with a specific time or range of time during exhalation, which may be determined from an output of sensor(s) 108.

In some embodiments, valve control module 116 is configured to control valve 106 according to the functionality of the particular therapy device being used. For example, if the particular device forces a flow of gas to the user, valve 106 should remain open during that forced flow. The valve control module 116, in accordance with some embodiments, is configured to provide information to one or more other components of respiratory treatment device 102 or system 100 relating to when valve 106 is open or closed.

The sensor control module 118 is configured to control sensor(s) 108 and/or regulate when signals provided by sensor(s) 108 are read. According to some embodiments, controlling sensor(s) 108 includes causing sensor(s) 108 to sense or obtain information associated with one or more characteristics of the exhaled gas in coordination with the subject exhaling and/or valve 106 temporarily interrupting the flow of the exhaled gas communicated by conduit 104.

The airway impedance monitoring module 120 is configured to determine an impedance metric of the airway of the subject. Such a determination may be made based on the signal (or the information conveyed thereby) provided by sensor(s) 108 during the one or more exhalations for which gas flow through the flow path is affected by the first valve. In some embodiments, determining an impedance metric may include determining a volume of inhaled gas based on the signal (or the information conveyed thereby) provided by sensor(s) 108 during the one or more inhalations. Some examples of the impedance metric include an airway resistance, an airway capacitance, and/or other impedance metrics associated with the airway of the subject. In some embodiments, the airway impedance monitoring module 120 is configured to determine the reliability of the information conveyed by the signal provided by sensor(s) 108. For example, according to some embodiments, if the exhalation is forced, rather than relaxed, the information may not be valid. As another example, if subsequent measurements show high variability, the information may not be valid, according to some embodiments. The airway impedance monitoring module 120 may utilize one or more functional models, in conjunction with the information conveyed by the signal provided by sensor(s) 108, to determine an impedance metric of the airway of the subject.

Figure 2:
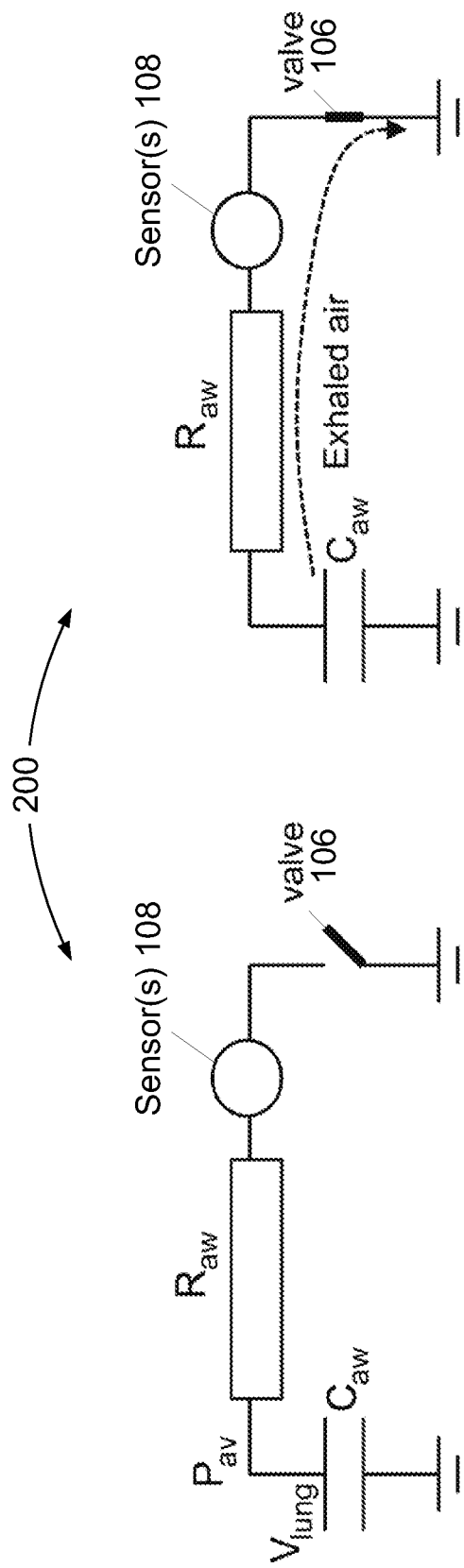
FIGS. 2A and 2B illustrate a functional airway impedance measurement model corresponding to one or more embodiments where the system of FIG. 1 includes an interrupter valve.

FIGS. 2A and 2B illustrate a functional airway impedance measurement model 200 corresponding to one or more embodiments where system 100 includes an interrupter valve. The airway impedance monitoring module 120 may utilize functional airway impedance measurement model 200 to determine an impedance metric of the airway of the subject. According to functional airway impedance measurement model 200, $R_{aw}$ represents airway resistance, $C_{aw}$ represents airway capacitance, $P_{av}$ represents alveolar pressure, and $V_{lung}$ represents gas stored in the lungs of the subject. In FIG. 2A, valve 106 does not permit gas can be exhaled from the lungs of the subject. Because of this, the pressure measured by sensor(s) 108, after equilibrium is reached, is expected to be equivalent to the alveolar pressure. After valve 106 is opened, as depicted in FIG. 2B, gas stored in the lungs is exhaled and the amount of exhaled gas is recorded by sensor(s) 108. By monitoring pressure variation and/or flow variation after (or before) interruption of the exhaled gas, and by estimating the initial alveolar pressure, the resistance and capacitance of the airway of the subject can be estimated. In some embodiments, estimating capacitance may include estimating changes in alveaolar pressure due to muscle activity, which is not represented in FIGS. 2A and 2B, but could be represented as a pressure source in series with the lung capacitance. Estimating the resistance and capacitance of the airway of the subject may include evaluating a flow waveform and/or a pressure waveform before, during, and/or after occlusion.

Figure 3:
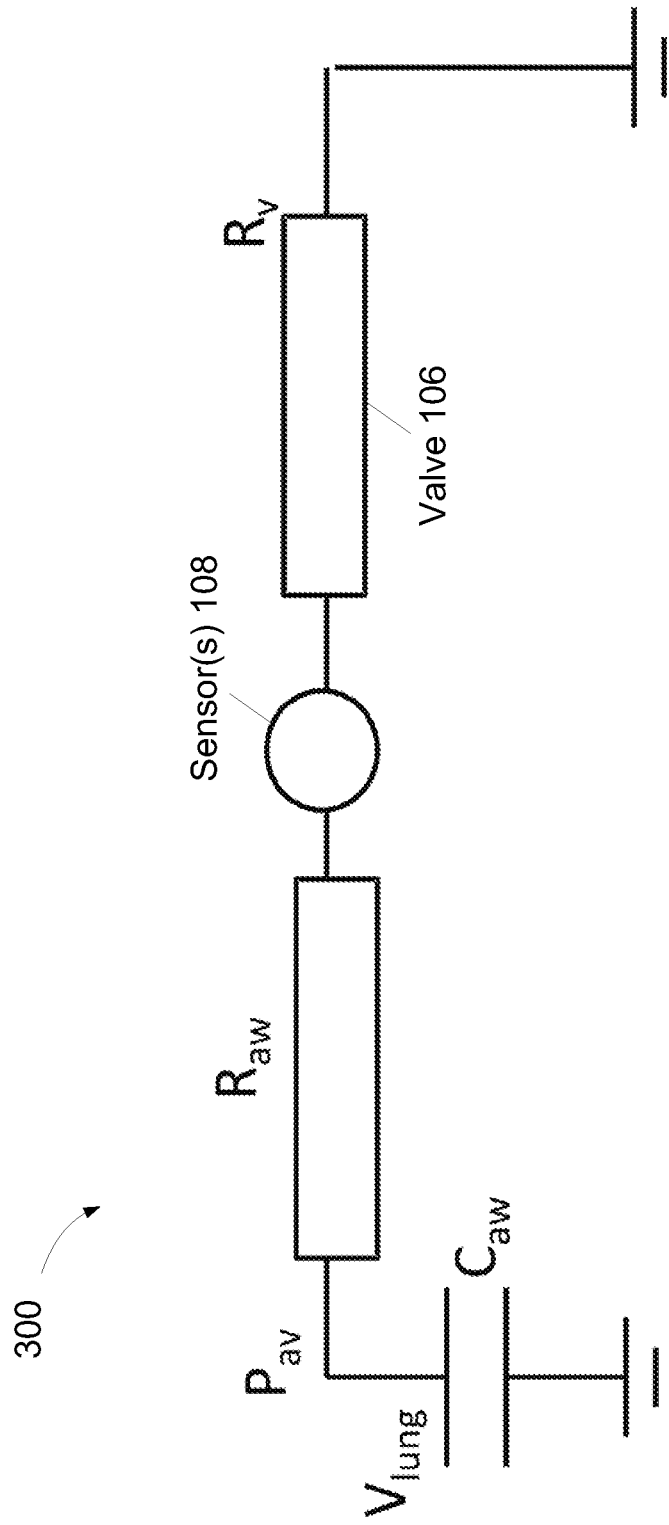
FIG. 3 illustrates a function airway impedance measurement model corresponding to one or more embodiments where the system of FIG. 1 includes a passive valve having a predetermined oscillation frequency.

FIG. 3 illustrates a function airway impedance measurement model 300 corresponding to one or more embodiments where system 100 includes a passive valve having a predetermined oscillation frequency. The airway impedance monitoring module 120 may utilize functional airway impedance measurement model 200 to determine an impedance metric of the airway of the subject. According function airway impedance measurement model 300, the differential equation controlling system 100 may be written as:

$$I = -C_{aw}\frac{dR_{aw}I}{dt} - C_{aw}\frac{dIR_v}{dt}, \quad (\text{EQN. 1})$$

where I represents the flow of exhaled gas sensed by sensor(s) 108. Assuming $R_{aw}$ to be constant and assuming the valve resistance $R_v$ to vary with time when subject to a flow of gas (and resonating or oscillating at a given frequency much higher than the frequency component of I in the absence of a valve), the two differential terms of EQN. 1 can be separated based on frequency. Therefore, solutions for low and high frequencies can be separately determined, respectively, as:

$$I_{LF} = -C_{aw}\frac{dR_{aw}I_{LF}}{dt}, \quad (\text{EQN. 2})$$

and $$I_{HF} = -C_{aw}\frac{dR_v I_{HF}}{dt}. \quad (\text{EQN. 3})$$

The resistance of the valve $R_v$ can be determined based on pressure and/or flow measurements obtained via sensor(s) 108, and can be written as:

$$R_v(I) = \frac{P}{I}, \quad (\text{EQN. 4})$$

where P represents the pressure determined via sensor(s) 108 referred to atmospheric pressure. Given these equations and the flow and pressure determined via sensor(s) 108, the value of $C_{aw}$ can be determined from the high frequency differential equation (i.e., EQN. 3). Is then possible to use the value of $C_{aw}$ to solve the low frequency differential equation (i.e., EQN 2) and determine $R_{aw}$. If valve(s) 106 have a non-negligible resistance in the low-frequency domain, that resistance can be calibrated and subtracted from the computed $R_{aw}$ value.

Referring again to FIG. 1, compliance monitoring module 122 is configured to monitor compliance of the subject using respiratory treatment device 102. Monitoring compliance may be based on the information conveyed by the signal provided by sensor(s) 108 and/or based on other information. Monitoring compliance of the subject, in one embodiment, includes characterizing the usage of respiratory treatment device 102 by the subject with respect to a usage goal, monitoring amount of usage, monitoring flow and/or pressure during usage, and/or monitoring or characterizing other aspects of usage. This may include determining whether the usage of respiratory treatment device 102 by the subject has met or exceeded the usage goal. Characterization of usage with respect to a usage goal by compliance monitoring module 122 may be made on an epoch and/or era basis. For example, to monitor compliance on an epoch basis, compliance monitoring module 122 compares usage during a given epoch with a usage goal for the given epoch. To monitor compliance on an era basis, compliance monitoring module 122 compares usage during a given era with an era goal.

Compliance may be monitored by compliance monitoring module 122 for time periods (e.g., epochs, eras, etc.) that have passed and/or for time periods that are currently occurring. For example, in the middle of a given epoch, compliance monitoring module 122 determines a characterization of the usage by the subject with the usage goal for the given epoch by comparing the current amount of usage by the subject in the given epoch with the usage goal for the given epoch. The usage goal may be prorated based on the current time that has passed within the given epoch, or current usage may be compared against the full usage goal even though the given epoch has not yet been concluded.

According to some embodiments, system 100 and/or the respiratory treatment device 102 includes electronic storage 124. Electronic storage 124 comprises electronic storage media that electronically stores information. The electronic storage media of electronic storage 124 may include one or both of system storage that is provided integrally (i.e., substantially non-removable) with system 100 and/or respiratory treatment device 102, and/or removable storage that is removably connectable to system 100 and/or respiratory treatment device 102 via, for example, a port (e.g., a USB port, a firewire port, etc.) or a drive (e.g., a disk drive, etc.). Electronic storage 124 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 124 may include one or more virtual storage resources (e.g., cloud storage, a virtual private network, and/or other virtual storage resources). Electronic storage 124 may store software algorithms, information determined by processor(s) 110 and/or other information that enables system 100 and/or respiratory treatment device 102 to function as described herein.

Processor(s) 110 is configured to provide information processing capabilities in system 100 and/or respiratory treatment device 102. As such, processor(s) 110 may include one or more of a digital processor, an analog processor, a digital circuit designed to process information, an analog circuit designed to process information, a state machine, and/or other mechanisms for electronically processing information. Although processor(s) 110 is shown in FIG. 1 as a single entity, this is for illustrative purposes only. In some embodiments, processor(s) 110 may include a plurality of processing units. These processing units may be physically located within the same device, or processor(s) 110 may represent processing functionality of a plurality of devices operating in coordination. The processor(s) 110 may be configured to execute modules 116, 118, 120, 122, and/or other modules by software; hardware; firmware; some combination of software, hardware, and/or firmware; and/or other mechanisms for configuring processing capabilities on processor(s) 110.

It should be appreciated that although modules 116, 118, 120, and 122 are illustrated in FIG. 1 as being co-located within a single processing unit, in embodiments in which processor(s) 110 includes multiple processing units, one or more of modules 116, 118, 120, and/or 122 may be located remotely from the other modules. The description of the functionality provided by the different modules 116, 118, 120, and/or 122 described below is for illustrative purposes, and is not intended to be limiting, as any of modules 116, 118, 120, and/or 122 may provide more or less functionality than is described. For example, one or more of modules 116, 118, 120, and/or 122 may be eliminated, and some or all of its functionality may be provided by other ones of modules 116, 118, 120, and/or 122. As another example, processor(s) 110 may be configured to execute one or more additional modules that may perform some or all of the functionality attributed below to one of modules 116, 118, 120, and/or 122.

Figure 4B:
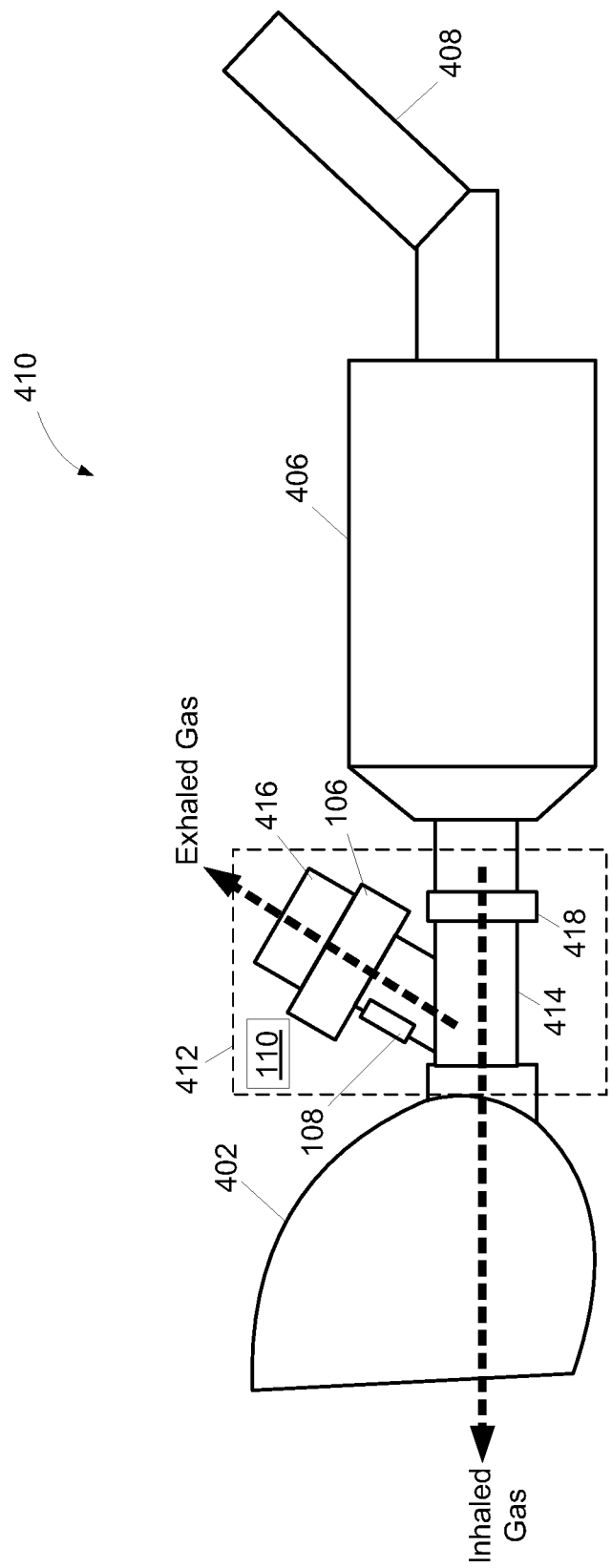

FIGS. 4A, 4B, 4C, and 4D illustrate exemplary embodiments of airway impedance measurement capabilities integrated with a respiratory treatment device. More specifically, FIG. 4A illustrates an inhaler apparatus 400. As depicted in FIG. 4A, inhaler apparatus 400 includes a mask 402, an airway impedance measurement apparatus 404, a valved holding chamber 406, an inhaler 408, and/or other components. The mask 402 is configured to provide fluid communication between inhaler apparatus 400 and an airway of a subject using inhaler apparatus 400. The mask 402 may be the same or similar to respiration interface 112 described in connection with FIG. 1. The airway impedance measurement apparatus 404 may be the same or similar to system 100 described in connection with FIG. 1. The airway impedance measurement apparatus 404 includes conduit 104, valve 106, sensor(s) 108, and processor(s) 110. The airway impedance measurement apparatus 404 is configured such that inhaled and exhaled gas are communicated via the same path through conduit 104 and valve 106. The inhaler 408 may be configured to store and/or dispense a breathable substance (e.g., a drug). The valved holding chamber 406 may be configured to facilitate an intermediary state in an inhalation process where a breathable substance is dispensed into valved holding chamber 406 and then inhaled by the subject. According to some embodiments, valved holding chamber 406 is omitted from inhaler apparatus 400.

Figure 4C:
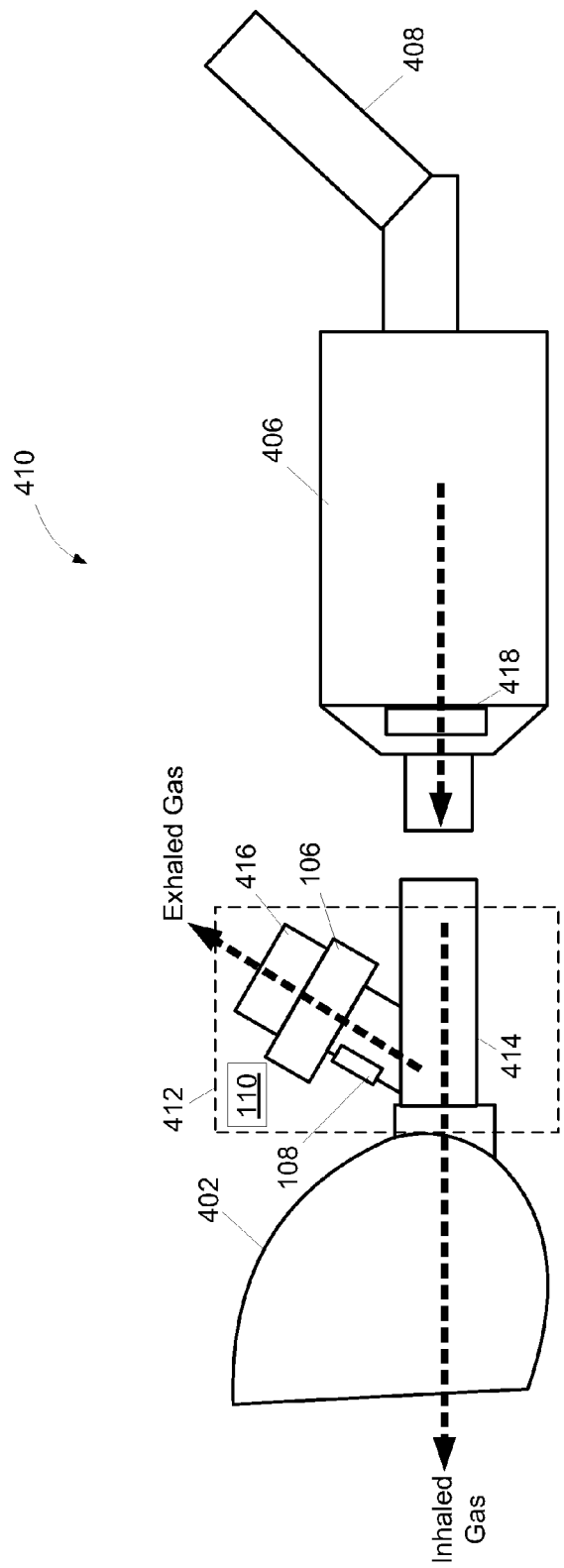

FIG. 4B illustrates an inhaler apparatus 410. As depicted in FIG. 4B, inhaler apparatus 410 includes mask 402, an airway impedance measurement apparatus 412, valved holding chamber 406, inhaler 408, and/or other components. The airway impedance measurement apparatus 412 may be the same or similar to system 100 described in connection with FIG. 1. The airway impedance measurement apparatus 412 includes conduit (e.g., conduit 104), valve 106, sensor(s) 108, processor(s) 110, and/or other components. The airway impedance measurement apparatus 412 is configured such that inhaled and exhaled gas are communicated via different paths through the conduit. In airway impedance measurement apparatus 412, the conduit includes a first branch 414 and a second branch 416. The first branch 414 includes a one-way valve 418 disposed therein. In some embodiments, one-way valve 418 is a preexisting component of valved holding chamber 406. The one-way valve 418 is configured such that inhaled gas is communicated by first branch 414 and exhaled gas is prevented from being communicated by first branch 414. The second branch 416 includes valve 106 disposed therein. Gas exhaled by the subject is communicated via branch 416 of the conduit. In inhaler apparatus 410, medication and/or other breathable substance is not blocked by valve 106 and/or sensor(s) 108 because they are not in the stream of inhaled gas. In some embodiments, valve 106 included in inhaler apparatus 410 is configured to prevent gas from being inhaled via branch 416. FIG. 4C depicts an alternative embodiment of inhaler apparatus 410 in which impedance measurement apparatus 412 is connected to detachable mask 402 while one-way valve 418 is part of valved holding chamber 406. In some embodiments, one-way valve 418 is also connected to detachable mask 402 such that airway impedance measurement apparatus 412 can be used in combination with inhaler 408 and/or as a stand-alone device.

Figure 4D:
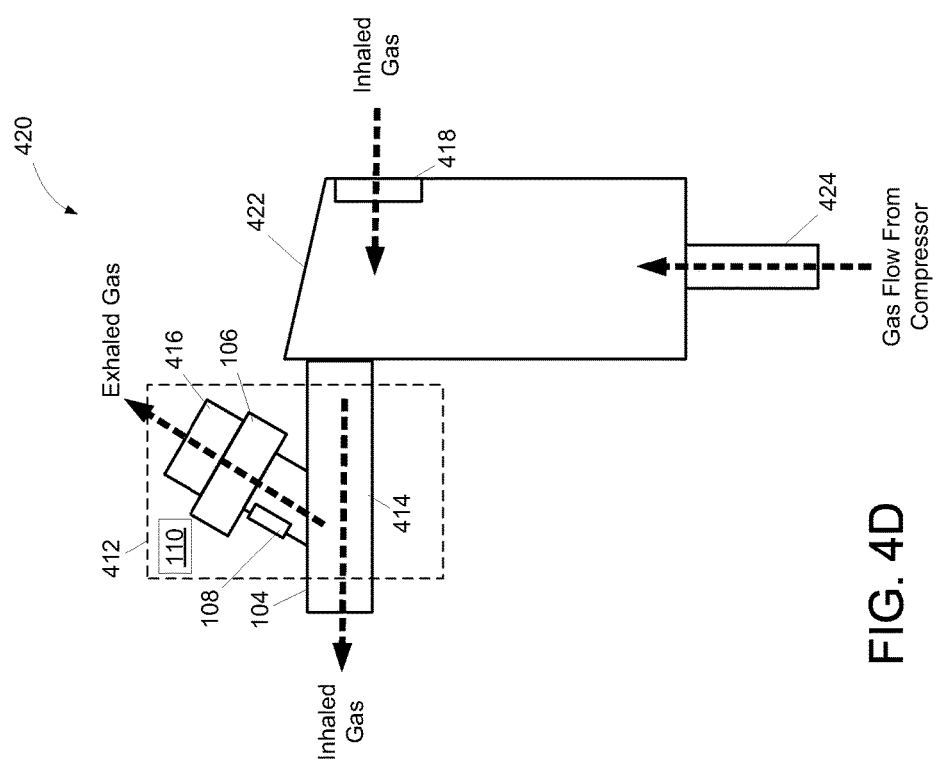

FIG. 4D illustrates an nebulizer apparatus 420. As depicted in FIG. 4D, nebulizer apparatus 420 includes airway impedance measurement apparatus 412, nebulizer handset 422, and/or other components. The airway impedance measurement apparatus 412 may be the same or similar to system 100 described in connection with FIG. 1. The airway impedance measurement apparatus 412 includes a conduit (e.g., conduit 104), valve 106, sensor(s) 108, processor(s) 110, and/or other components. The airway impedance measurement apparatus 412 is configured such that inhaled and exhaled gas are communicated via different paths through conduit 104. In airway impedance measurement apparatus 412, the conduit includes a first branch 414 and a second branch 416. The first branch 414 is communicatively coupled (may be removable) with nebulizer handset 422, which includes a one-way valve 418. In some embodiments, one-way valve 418 is a preexisting component of nebulizer handset 422. The one-way valve 418 is configured such that inhaled gas is communicated by nebulizer handset 422 and first branch 414. The second branch 416 includes valve 106 disposed therein. Gas exhaled by the subject is communicated via branch 416 of the conduit. In nebulizer apparatus 420, medication and/or other breathable substance is not blocked by valve 106 and/or sensor(s) 108 because they are not in the stream of inhaled gas. In some embodiments, valve 106 included in nebulizer apparatus 420 is configured to prevent gas from being inhaled via branch 416. A compressed flow of gas is introduced at intake 424, for example, from a compressor and/or other source of compressed gas. The intake 424 may include a one-way valve (not depicted) such that exhaled gas cannot flow out of intake 424. In embodiments where there is no valve disposed at the interface of conduit 104 and nebulizer handset 422 (e.g., the embodiment illustrated in FIG. 4D), the effect of the cavity of nebulizer handset 422 may be calibrated and/or taken into account when determining airway impedance. In embodiments where gas flow introduced via intake 424 is not stopped during measurement of the characteristic(s) of exhaled gas, the effect of that gas flow may be calibrated and/or taken into account when determining airway impedance.

FIG. 500 illustrates a method for measuring airway impedance of a subject using a respiratory treatment device, in accordance with one or more embodiments. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a flow of inhaled gas and a flow of exhaled gas are communicated between the respiratory treatment device and an airway of the subject using the respiratory treatment device. According to some embodiments, a conduit that is the same or similar to conduit 104 performs operation 502.

At an operation 504, the flow of exhaled gas is affected. In some embodiments, affecting the flow of exhaled gas includes temporarily interrupting the flow of exhaled gas. According to some embodiments, affecting the flow of exhaled gas includes providing a time-variable resistance to the flow of exhaled gas. A valve that is the same or similar to valve 106 performs operation 504, in accordance with one or more embodiments.

At an operation 506, a signal is provided that conveys information associated with one or more characteristics of gas exhaled by the subject while the flow of exhaled gas is affected or unaffected. Such characteristics may include one or more of a flow rate of communicated gas, a gas pressure, a volume or amount of communicated gas communicated, and/or other characteristics of the exhaled gas. In some embodiments, one or more sensors that are the same or similar to sensor(s) 108 perform operation 506.

At an operation 508, an impedance metric is determined of the airway of the subject based on the information conveyed by the signal provided at operation 506. Some examples of the impedance metric include an airway resistance, an airway capacitance, and/or other impedance metrics associated with the airway of the subject. An airway impedance monitoring module that is the same or similar to airway impedance monitoring module 120 is executed to perform operation 508, according to some embodiments.

At an operation 510, compliance is monitored of the subject using the respiratory treatment device. Monitoring compliance may be based on the information conveyed by the signal provided at operation 506 and/or based on other information. In some embodiments, a compliance monitoring module that is the same or similar to compliance monitoring module 122 is executed to perform operation 510.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system integrated with a respiratory treatment device and configured to measure airway impedance, the system comprising:
    a conduit configured to provide a flow path for gas toward and away from an airway of a subject using the respiratory treatment device during inhalation and exhalation, respectively, the conduit including a first branch configured to communicate an inhaled gas toward the airway of the subject and a second branch configured to communicate an exhaled gas away from the airway of the subject to an ambient environment;
    a first valve disposed within the second branch of the conduit to affect a gas flow through the flow path formed by the conduit such that the exhaled gas is communicated via the second branch;
    a second valve disposed within the first branch of the conduit such that the inhaled gas is communicated by the first branch and the exhaled gas is prevented from being communicated by the first branch, the second valve comprising a one-way valve;
    one or more sensors disposed within the conduit and configured to provide a signal conveying information associated with one or more characteristics of gas in the flow path formed by the conduit while the gas flow through the flow path is affected or unaffected by the first valve; and
    one or more processors configured by machine readable instructions to:
        determine an impedance metric of the airway of the subject based on the signal provided by the one or more sensors during the one or more exhalations for which the gas flow through the flow path is affected or unaffected by the first valve, the impedance metric related to a pressure of gas in the flow path indicative of airway resistance to flow; and
        cause the first valve, during the impedance metric determination and until the pressure of gas in the flow path becomes stable, to change a level of gas flow through the flow path.

2. The system of claim 1, wherein the first valve comprises a passive valve having a predetermined oscillation frequency, the passive valve being configured to affect the gas flow through the flow path formed by the conduit by providing a time-variable resistance to the gas flow through the flow path formed by the conduit during exhalation.

3. The system of claim 1, wherein the first valve comprises an interrupter valve configured to affect the gas flow through the flow path formed by the conduit by temporarily interrupting the gas flow through the flow path formed by the conduit during exhalation.

4. The system of claim 3, wherein the one or more characteristics of gas in the flow path formed by the conduit include:
    a flow rate of gas flow through the flow path during exhalation when the gas flow through the flow path formed by the conduit is uninterrupted by the interrupter valve; and
    an interruption pressure of gas in the flow path during exhalation when the gas flow through the flow path formed by the conduit is interrupted by the interrupter valve.

5. The system of claim 3, wherein the one or more processors are further configured to control the interrupter valve so as to synchronize affecting the gas flow with a specific time or a range of time during exhalation.

6. A method for measuring airway impedance of a subject using a respiratory treatment device, the method comprising:
    providing a flow path for gas toward and away from an airway of a subject using the respiratory treatment device during inhalation and exhalation, respectively, wherein providing the flow path for gas toward and away from the airway of the subject includes communicating a flow of an inhaled gas toward the airway of the subject via a first branch of a conduit, preventing a flow of an exhaled gas from being communicated via the first branch of the conduit, the first branch of the conduit having a one way valve disposed therein, and communicating the flow of the exhaled gas away from the airway of the subject to an ambient environment via a second branch of the conduit, the second branch of the conduit having a first valve disposed therein;
    affecting a gas flow through the flow path;
    providing a signal conveying information associated with one or more characteristics of gas in the flow path while the gas flow through the flow path is affected or unaffected;
    determining an impedance metric of the airway of the subject based on the signal during the one or more exhalations for which gas flow through the flow path is affected or unaffected, the impedance metric related to a pressure of gas in the flow path indicative of airway resistance to flow; and
    causing the first valve, during the impedance metric determination and until the pressure of gas in the flow path becomes stable, to change a level of gas flow through the flow path.

7. The method of claim 6, wherein affecting the gas flow through the flow path includes providing a time-variable resistance to the gas flow through the flow path.

8. The method of claim 6, wherein affecting the gas flow through the flow path includes temporarily interrupting the gas flow through the flow path during exhalation.

9. The method of claim 8, wherein the one or more characteristics of the gas in the flow path include:
    a flow rate of the gas flow through the flow path during exhalation when the gas in the flow path is uninterrupted; and
    an interruption pressure of the gas in the flow path during exhalation when the gas in the flow path is interrupted.

10. The method of claim 8, wherein affecting the gas flow through the flow path is synchronized with a specific time or a range of time during exhalation.

11. A system integrated with a respiratory treatment device and configured to measure airway impedance, the system comprising:
    fluid communication means configured to provide a flow path for gas toward and away from an airway of a subject using the respiratory treatment device during inhalation and exhalation, respectively;
    first valve means disposed within the fluid communication means to affect a gas flow through the flow path formed by the fluid communication means,
    wherein the fluid communication means includes first branch means configured to communicate an inhaled gas toward the airway of the subject and second branch means configured to communicate an exhaled gas away from the airway of the subject to an ambient environment, the first branch means having a one-way valve means disposed therein such that the inhaled gas is communicated by the first branch means and exhaled gas is prevented from being communicated by the first branch means, the second branch means having the first valve means disposed therein;

sensing means disposed within the fluid communication means and configured to provide a signal conveying information associated with one or more characteristics of gas in the flow path formed by the fluid communication means while the gas flow through the flow path is affected or unaffected by the first valve means;

processing means configured by machine readable instructions to:

determine an impedance metric of the airway of the subject based on the signal provided by the sensing means during the one or more exhalations for which the gas flow through the flow path is affected or unaffected by the first valve means, the impedance metric related to a pressure of gas in the flow path indicative of airway resistance to flow; and cause the first valve, during the impedance metric determination and and until the pressure of gas in the flow path becomes stable, to change a level of gas flow through the flow path.

12. The system of claim 11, wherein the first valve means includes a passive valve means having a predetermined oscillation frequency, the passive valve means being configured to affect the gas flow through the flow path formed by the fluid communication means by providing a time-variable resistance to the gas flow through the flow path formed by the fluid communication means during exhalation.

13. The system of claim 11, wherein the first valve means includes an interrupter valve means configured to affect the gas flow through the flow path formed by the fluid communication means by temporarily interrupting the gas flow through the flow path formed by the fluid communication means during exhalation.

14. The system of claim 13, wherein the one or more characteristics of the gas in the flow path include:

a flow rate of gas flow through the flow path during exhalation when the gas flow through the flow path formed by the fluid communication means is uninterrupted by the interrupter valve means; and an interruption pressure of gas in the flow path during exhalation when the gas flow through the flow path formed by the fluid communication means is interrupted by the interrupter valve means.

15. The system of claim 1, wherein determining the impedance metric of the airway further comprises:

determining one or more subsequent impedance metrics based on the signal;

determining a variance of the one or more subsequent impedance metrics; and determining a reliability of the signal based on the variance.

16. The method of claim 6, wherein determining the impedance metric of the airway further comprises:

determining one or more subsequent impedance metrics based on the signal;

determining a variance of the one or more subsequent impedance metrics; and determining a reliability of the signal based on the variance.

17. The system of claim 11, wherein determining the impedance metric of the airway further comprises:

determining one or more subsequent impedance metrics based on the signal;

determining a variance of the one or more subsequent impedance metrics; and determining a reliability of the signal based on the variance.

18. The system of claim 1, wherein the one or more processors are further configured to:

detect a pressure of the exhaled gas during the one or more exhalations based on the signal;

determine a stability of the pressure based on the detected pressure during the one or more exhalations; and cause the first valve to change the level of gas flow through the flow path responsive to the detected pressure of the exhaled gas becoming stable over time.

19. The method of claim 6, wherein the method further comprises:

detecting a pressure of the exhaled gas during the one or more exhalations based on the signal;

determining a stability of the pressure based on the detected pressure during the one or more exhalations; and causing the first valve to change the level of gas flow through the flow path responsive to the detected pressure of the exhaled gas becoming stable over time.

20. The system of claim 11, wherein the processing means is further configured by machine readable instructions to:

detect a pressure of the exhaled gas during the one or more exhalations based on the signal;

determine a stability of the pressure based on the detected pressure during the one or more exhalations; and cause the first valve to change the level of gas flow through the flow path responsive to the detected pressure of the exhaled gas becoming stable over time.

* * * * *